United States Patent
Do et al.

(10) Patent No.: US 11,615,879 B2
(45) Date of Patent: Mar. 28, 2023

(54) SYSTEM AND METHOD FOR AUTOMATED LABELING AND ANNOTATING UNSTRUCTURED MEDICAL DATASETS

(71) Applicant: THE GENERAL HOSPITAL CORPORATION, Boston, MA (US)

(72) Inventors: Synho Do, Lexington, MA (US); Jung Hwan Cho, Dracut, MA (US)

(73) Assignee: The General Hospital Corporation, Boston, MA (US)

( * ) Notice: Subject to any disclaimer, the term of this patent is extended or adjusted under 35 U.S.C. 154(b) by 293 days.

(21) Appl. No.: 16/645,240

(22) PCT Filed: Sep. 10, 2018

(86) PCT No.: PCT/US2018/050173
§ 371 (c)(1),
(2) Date: Mar. 6, 2020

(87) PCT Pub. No.: WO2019/051356
PCT Pub. Date: Mar. 14, 2019

(65) Prior Publication Data
US 2020/0285906 A1   Sep. 10, 2020

Related U.S. Application Data

(60) Provisional application No. 62/555,799, filed on Sep. 8, 2017, provisional application No. 62/555,767, filed on Sep. 8, 2017.

(51) Int. Cl.
*G16H 30/00* (2018.01)
*G16H 30/40* (2018.01)
(Continued)

(52) U.S. Cl.
CPC ............ *G16H 30/40* (2018.01); *G06K 9/628* (2013.01); *G06K 9/6257* (2013.01);
(Continued)

(58) Field of Classification Search
CPC ........ G16H 30/40; G16H 20/40; G16H 15/00; G06V 20/20; G06V 10/42;
(Continued)

(56) References Cited

U.S. PATENT DOCUMENTS

2008/0292055 A1   11/2008 Boone
2013/0338496 A1   12/2013 Hielscher
(Continued)

OTHER PUBLICATIONS

American Association of Physicists in Medicine. Size-specific dose estimates (SSDE) in pediatric and adult body CT Examinations: report of AAPM Task Group 204. College Park, Md: American Association of Physicists in Medicine, 2011.
(Continued)

*Primary Examiner* — Khai M Nguyen
(74) *Attorney, Agent, or Firm* — Quarles & Brady LLP

(57) ABSTRACT

Supervised and unsupervised learning schemes may be used to automatically label medical images for use in deep learning applications. Large labeled datasets may be generated from a small initial training set using an iterative snowball sampling scheme. A machine learning powered automatic organ classifier for imaging datasets, such as CT datasets, with a deep convolutional neural network (CNN) followed by an organ dose calculation is also provided. This technique can be used for patient-specific organ dose estimation since the locations and sizes of organs for each patient can be calculated independently.

16 Claims, 11 Drawing Sheets

(51) Int. Cl.
G06K 9/62 (2022.01)
G06N 3/084 (2023.01)
G06N 7/00 (2023.01)
G16H 20/40 (2018.01)
G16H 15/00 (2018.01)
G06V 10/42 (2022.01)
G06V 10/75 (2022.01)
G06V 20/20 (2022.01)

(52) U.S. Cl.
CPC ......... *G06K 9/6259* (2013.01); *G06K 9/6262* (2013.01); *G06K 9/6277* (2013.01); *G06N 3/084* (2013.01); *G06N 7/005* (2013.01); *G06V 10/42* (2022.01); *G06V 10/751* (2022.01); *G06V 20/20* (2022.01); *G16H 15/00* (2018.01); *G16H 20/40* (2018.01); *G06V 2201/031* (2022.01)

(58) Field of Classification Search
CPC ........... G06V 2201/031; G06K 9/6257; G06K 9/6259; G06K 9/6262; G06K 9/6277; G06K 9/628; G06N 3/084; G06N 7/005
See application file for complete search history.

(56) References Cited

U.S. PATENT DOCUMENTS

| | | | |
|---|---|---|---|
| 2014/0270053 A1* | 9/2014 | Larson | A61B 6/545 378/4 |
| 2016/0259888 A1 | 9/2016 | Liu et al. | |
| 2017/0200265 A1 | 7/2017 | Bhaskar et al. | |
| 2017/0213339 A1* | 7/2017 | Hibbard | G06T 7/11 |
| 2017/0245825 A1 | 8/2017 | Star-Lack et al. | |
| 2021/0073987 A1* | 3/2021 | Tegzes | G06T 7/0012 |

OTHER PUBLICATIONS

Bauhs, J. A., et al. "CT dosimetry: comparison of measurement techniques and devices 1." Radiographics 28, No. 1 (2008): 245-253.
Criminisi, A, et al. "Decision forests with long-range spatial context for organ localization in CT volumes." In Medical Image Computing and Computer-Assisted Intervention (MICCAI), pp. 69-80. 2009.
Criminisi, A, et al. "Regression forests for efficient anatomy detection and localization in computed tomography scans." Medical image analysis 17, No. 8 (2013): 1293-1303.
Dennis Jr JE, et al: An adaptive nonlinear least-squares algorithm. ACM Transactions on Mathematical Software (TOMS) 7:348-368, 1981.
Doersch C: Tutorial on variational autoencoders. arXiv preprint arXiv:160605908, 2016.
Doshi J, et al.: Ensemble-based medical image labeling via sampling morphological appearance manifolds. Proc. MICCAI Challenge Workshop on Segmentation: Algorithms, Theory and Applications Nagoya, Japan. 2013.
Figueroa RL, et al: Predicting sample size required for classification performance. BMC medical informatics and decision making 12:8, 2012.
Gao M, et al: Simplified labeling process for medical image segmentation. Proc. International Conference on Medical Image Computing and Computer-Assisted Intervention. 2012.
Gong T, et al: Automatic labeling and classification of brain CT images. Proc. Image Processing (ICIP), 2011 18th IEEE International Conference on Image Processing.
Gueld, M. O., et al. "Quality of DICOM header information for image categorization." In Medical Imaging 2002, pp. 280-287. International Society for Optics and Photonics, 2002.
Hua K-L, et al: Computer-aided classification of lung nodules on computed tomography images via deep learning technique. OncoTargets and therapy 8:2015-2022, 2014.
International Searching Authority, International Search Report and Written Opinion for application PCT/US2018/050173. dated Nov. 29, 2018.
International Searching Authority, International Search Report and Written Opinion for application PCT/US2018/050177. dated Nov. 19, 2018.
Jones N: The learning machines. Nature 505:146, 2014.
Ingma DP, et al: Auto-encoding variational bayes. arXiv preprint arXiv:13126114, 2013.
McCollough, C. H. "CT dose: how to measure, how to reduce." Health physics 95, No. 5 (2008): 508-517.
Roth HR, et al. "Anatomy-specific classification of medical images using deep convolutional nets." In 2015 IEEE 12th International Symposium on Biomedical Imaging (ISBI), pp. 101-104. IEEE, 2015.
Russakovsky O, et al.: Imagenet large scale visual recognition challenge. International Journal of Computer Vision 115:211-252, 2015.
Shakeri M, et al.: Sub-cortical brain structure segmentation using F-CNN's. Proc. Biomedical Imaging (ISBI), 2016 IEEE 13th International Symposium on Biomedical Imaging (ISBI).
Shiraishi J, et al: Computer-aided diagnosis and artificial intelligence in clinical imaging. Proc. Seminars in nuclear medicine: 2011.
Smith-Bindman, R, et al. "Rising use of diagnostic medical imaging in a large integrated health system." Health affairs 27.6 (2008): 1491-1502.
Szegedy C, et al.: Going deeper with convolutions. Proc. Proceedings of the IEEE Conference on Computer Vision and Pattern Recognition. 2015.
Vajda S, et al: Label the many with a few: Semi-automatic medical image modality discovery in a large image collection. Proc. Computational Intelligence in Healthcare and e-health (CICARE), 2014 IEEE Symposium Computational Intelligence in Healthcare and e-health (CICARE).
Yan Z, et al.: Bodypart recognition using multi-stage deep learning. Proc. International Conference on Information Processing in Medical Imaging. 2015.
Yan Z, et al.: Multi-instance deep learning: Discover discriminative local anatomies for bodypart recognition. IEEE transactions on medical imaging 35:1332-1343, 2016.
Ypsilantis P-P, et al.: Predicting response to neoadjuvant chemotherapy with PET imaging using convolutional neural networks. PloS one 10:e0137036, 2015.
Zhang L, et al: Automatic labeling of MR brain images by hierarchical learning of atlas forests. Medical physics 43:1175-1186, 2016.

* cited by examiner

SYSTEM AND METHOD FOR AUTOMATED LABELING AND ANNOTATING UNSTRUCTURED MEDICAL DATASETS

CROSS-REFERENCE TO RELATED APPLICATIONS

This application represents the national stage entry of PCT International Application No. PCT/US2018/050173 filed Sep. 10, 2018, which claims the benefit of U.S. Provisional Patent Application Ser. No. 62/555,799 filed on Sep. 8, 2017, and entitled "A methodology for automated labeling and annotation for unstructured big medical datasets," and U.S. Provisional Patent Application Ser. No. 62/555,767 filed on Sep. 8, 2017, and entitled "Method and apparatus of machine learning based personalized organ dose estimation incorporated herein by reference in their entirety.

STATEMENT REGARDING FEDERALLY SPONSORED RESEARCH

N/A

BACKGROUND

Diagnostic medical imaging has become central to the practice of modern medicine and diagnostic examination volume has increased during the past decade. Additionally, as systems have become more advanced with higher resolution, the number of images in a given study has also increased. The increased demand for diagnostic imaging also presents a growing risk for human error and delayed diagnosis. While computer aided detection (CADe) and diagnosis (CADx) systems can reduce such problems, they remain limited due to their reliance upon hand-crafted features. Deep-learning approaches sidestep this problem by extracting these features on their own. Recent advances in deep learning technology have enabled data-driven learning of nonlinear image filters and classifiers have improved detection and segmentation of multiple medical applications including brain infarcts, automated bone age analysis, and skin lesion classification. Despite these advances, large-scale and well-labeled training datasets for deep learning are essential for the networks to learn representative and hierarchical abstractions.

This labeling requirement is inherently difficult to meet in the medical domain where medical expertise is expensive, labeling is tedious and time-consuming, and examples of certain disease pathologies may be rare. Several automated annotation approaches have been attempted on brain CT, brain MR, and other biomedical image modalities with various feature representation, clustering, and classification algorithms. These approaches are limited because only low-level visual features such as color, edges, and color layouts are extracted. Even with higher-level feature extraction from MR voxels by hierarchical learning using two-layer random forests, segmentation performance is not generally better than features extracted by deep convolutional neural networks. Furthermore, all current methods of annotating medical images still require mid- to large-sized labeled image datasets for obtaining the trained model.

Axial image location classification is a fundamental step in multiple initial classification processes to classify the location of an image in a volumetric CT examination. Classifying the location is a challenging problem because the details of body regions can vary dramatically between patients, such as with brain gyral patterns, cervical vertebral anatomy, pulmonary vessels, and bowel distribution. Degenerative changes can also distort bony anatomy enough to confuse the network. As a result, large training data sets are common for algorithms to achieve sufficient accuracy.

Body-part recognition is also important in automatic medical image analysis as it is a prerequisite step for anatomy identification and organ segmentation. Accurate body-part classification facilitates organ detection and segmentation by reducing the search range for an organ of interest. Multiple techniques have been developed using multi-class random regression and decision forests to classify multiple anatomical structures ranging from 6-10 organs on tomographic (CT) scans. These classifiers can discriminate between similar structures such as the aortic arch and heart. However, these prior works focus on a general anatomical body part classification.

Thus, high-quality training data is important to training neural networks and unlock the potential for neural networks to truly improve the clinical use of medical images. However, creating high-quality training datasets is expensive and time-consuming.

SUMMARY OF THE DISCLOSURE

The present disclosure addresses the aforementioned drawbacks by providing a system and method for using supervised and unsupervised learning schemes to automatically label medical images for use in subsequent deep learning applications. The system can generate a large labeled dataset from a small initial training set using an iterative snowball sampling scheme. A machine-learning powered, automatic organ classifier for imaging datasets, such as CT datasets, with a deep convolutional neural network (CNN) followed by an organ dose calculation is also provided. This technique can be used for patient-specific organ dose estimation because the locations and sizes of organs for each patient can be calculated independently, rather than other simulation based methods.

In one configuration, a method is provided for automatically processing unstructured medical imaging data to generate classified images. The method includes acquiring medical image data of a subject and subjecting the medical image data of the subject to a neural network to generate classified image data. The method may also include comparing the classified image data to a confidence test, and upon determining that the classified image data does not pass the confidence test, subjecting the classified image data to a variational autoencoder (VAE) that implements a snowball sampling algorithm to refine the classified image data by representing features of the classified image data into latent space with a Gaussian distribution. In some configurations, this is repeated until the classified image data passes the confidence test. Annotated images may then be generated from the classified image data.

In one configuration, a method is provided for automatic labeling and annotation for unstructured medical datasets with snowball sampling. The method includes acquiring images of a region of a subject and labeling the images to generate a training dataset with the images. The method also includes training a network, such as a convolutional neural network, with the training dataset and classifying unlabeled images using the trained network. The method may also include determining if a performance threshold is exceeded for the classified images. The dataset may be refined if the threshold is not exceeded by using a variational autoencoder to label the unlabeled images to create labeled images and updating the dataset with the labeled images.

In one configuration, a system is provided for automatic labeling and annotation for unstructured medical datasets from medical images with snowball sampling. The system includes a computer system configured to: i) acquire images of a region of a subject and label the images to generate a training dataset with the images; ii) train a convolutional neural network with the training dataset; iii) classify unlabeled images using the trained network; iv) determine if a performance threshold is exceeded for the classified images; and v) refine the dataset if the threshold is not exceeded by using a variational autoencoder to label the unlabeled images to create labeled images and updating the dataset with the labeled images.

In one configuration, a method is provided for organ classification for unstructured medical datasets. The method includes acquiring images of a region of a subject and labeling the images to generate a training dataset with the images. The method may also include training a network, such as a convolutional neural network, with the training dataset. A region in the images may be classified using the trained network. The classified images may be segmented using the convolutional neural network to generate segmented images that distinguish between at least two different organs in the classified regions in the images. A report may be generated of a calculated radiation dose for at least one of the organs in the segmented images.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

The present disclosure provides systems and method for supervised and unsupervised learning schemes that may be used to automatically label medical images for use in deep learning applications. Large labeled datasets may be generated from a small initial training set using an iterative snowball sampling scheme. A machine learning powered automatic organ classifier for imaging datasets, such as CT datasets, with a deep convolutional neural network (CNN) followed by an organ dose calculation is also provided. This technique can be used for patient-specific organ dose estimation since the locations and sizes of organs for each patient can be calculated independently.

In one configuration, a desired classification accuracy may be achieved with a minimal labeling process. Using an iterative snowball sampling approach, a large medical image dataset may be annotated automatically with a smaller training subset. The automatic labeling system may include a variational autoencoder (VAE) for the purpose of feature representation, Gaussian mixture models (GMMs) for clustering and refining of mislabeled classes, and deep convolutional neural network (DCNN) for classification. The system and method can also quickly and efficiently identify an organ of interest at a higher accuracy when compared to current text-based body part information in digital imaging and communications in medicine (DICOM) headers. In one configuration, the method selects candidates, classifies them by the DCNN, and then fully refines them by learning features from a VAE and clustering the features by GMM.

Figure 1:
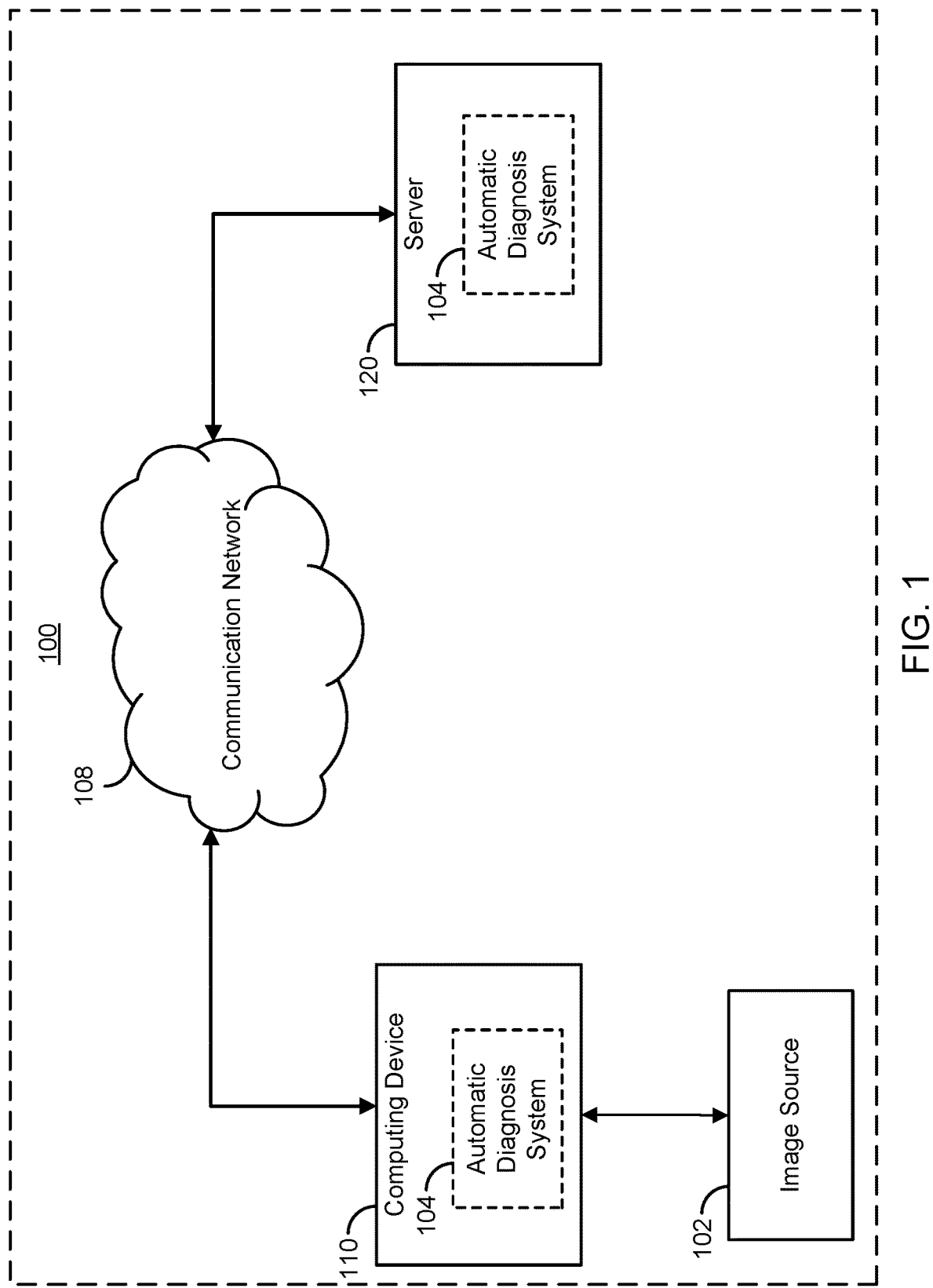
FIG. 1 is a schematic diagram of one system in accordance with the present disclosure.

Referring to FIG. 1, an example of a system 100 is shown for automatically labeling images using image data in accordance with some aspects of the disclosed subject matter. As shown in FIG. 1, a computing device 110 can receive multiple types of image data from an image source 102. In some configurations, the computing device 110 can execute at least a portion of an automatic image labelling system 104 to automatically determine whether a feature is present in images of a subject.

Additionally or alternatively, in some configurations, the computing device 110 can communicate information about image data received from the image source 102 to a server 120 over a communication network 108, which can execute at least a portion of the automatic image labelling system 104 to automatically determine whether a feature is present in images of a subject. In such configurations, the server 120 can return information to the computing device 110 (and/or any other suitable computing device) indicative of an output of the automatic image labelling system 104 to determine whether a feature is present or absent.

In some configurations, the computing device 110 and/or server 120 can be any suitable computing device or combination of devices, such as a desktop computer, a laptop computer, a smartphone, a tablet computer, a wearable computer, a server computer, a virtual machine being executed by a physical computing device, etc. In some configurations, the automatic image labelling system 104 can extract features from labeled (e.g., labeled as including a condition or disease, or normal) image data using a CNN trained as a general image classifier, and can perform a correlation analysis to calculate correlations between the features corresponding to the image data and a database. In some embodiments, the labeled data can be used to train a classification model, such as a support vector machine (SVM), to classify features as indicative of a disease or a condition, or as indicative of normal. In some configurations, the automatic image labelling system 104 can provide features for unlabeled image data to the trained classification model.

In some configurations, the image source 102 can be any suitable source of image data, such as an MRI, CT, ultrasound, PET, SPECT, x-ray, or another computing device (e.g., a server storing image data), and the like. In some configurations, the image source 102 can be local to the computing device 110. For example, the image source 102 can be incorporated with the computing device 110 (e.g., the computing device 110 can be configured as part of a device for capturing and/or storing images). As another example, the image source 102 can be connected to the computing device 110 by a cable, a direct wireless link, or the like. Additionally or alternatively, in some configurations, the image source 102 can be located locally and/or remotely from the computing device 110, and can communicate image data to the computing device 110 (and/or server 120) via a communication network (e.g., the communication network 108).

In some configurations, the communication network 108 can be any suitable communication network or combination of communication networks. For example, the communication network 108 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some configurations, the communication network 108 can be a local area network, a wide area network, a public network (e.g., the Internet), a private or semi-private network (e.g., a corporate or university intranet), other suitable type of network, or any suitable combination of networks. Communications links shown in FIG. 1 can each be any suitable communications link or combination of communications links, such as wired links, fiber optic links, Wi-Fi links, Bluetooth links, cellular links, etc.

Figure 2:
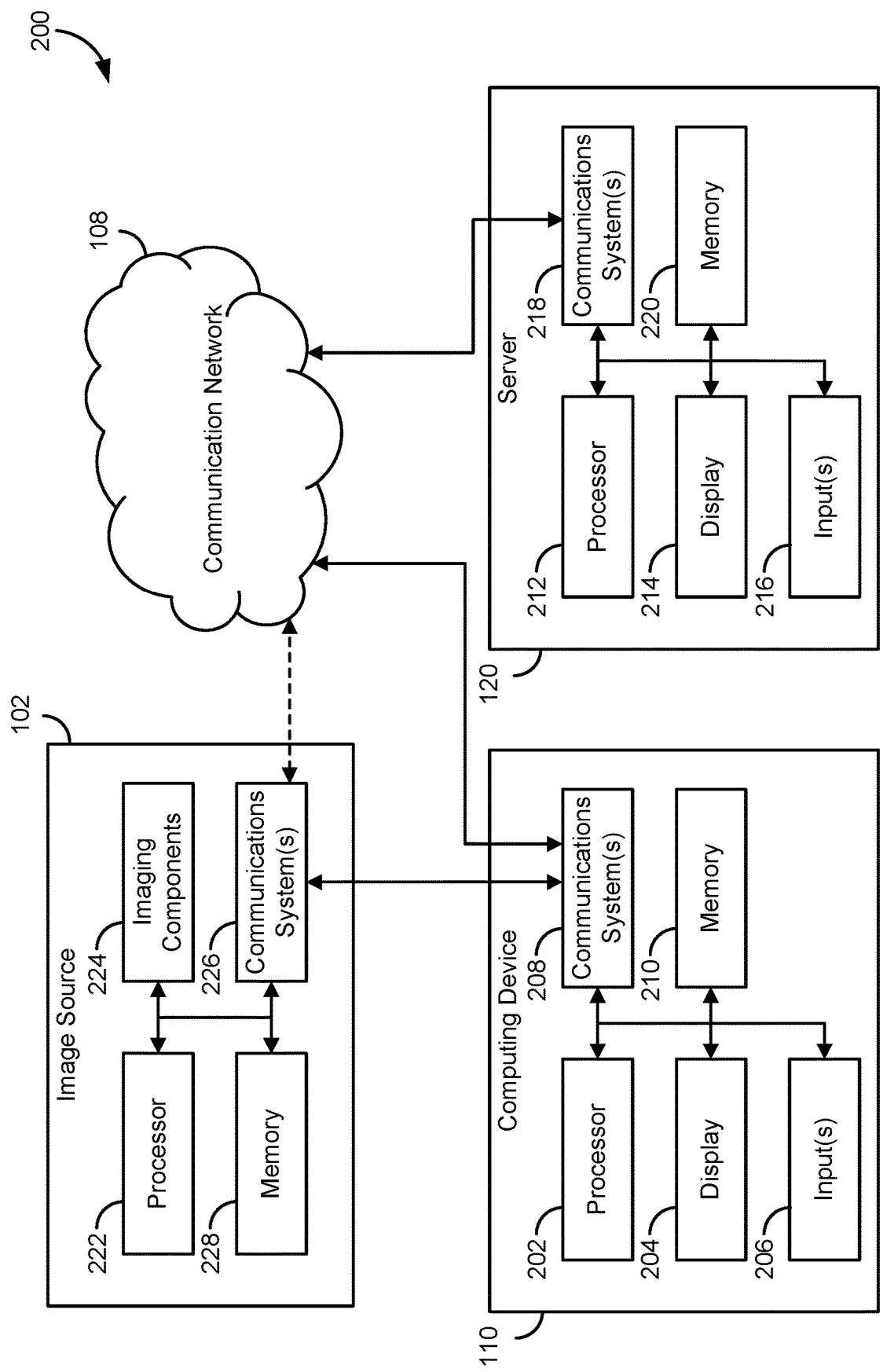
FIG. 2 is a schematic diagram showing further details of one, non-limiting example of the system of FIG. 1.

FIG. 2 shows an example of hardware 200 that can be used to implement the image source 102, computing device 110, and/or server 120 in accordance with some aspects of the disclosed subject matter. As shown in FIG. 2, in some configurations, the computing device 110 can include a processor 202, a display 204, one or more inputs 206, one or more communication systems 208, and/or memory 210. In some configurations, the processor 202 can be any suitable hardware processor or combination of processors, such as a central processing unit (CPU), a graphics processing unit (GPU), etc. In some configurations, the display 204 can include any suitable display devices, such as a computer monitor, a touchscreen, a television, etc. In some configurations, the inputs 206 can include any of a variety of suitable input devices and/or sensors that can be used to receive user input, such as a keyboard, a mouse, a touchscreen, a microphone, and the like.

In some configurations, the communications systems 208 can include a variety of suitable hardware, firmware, and/or software for communicating information over the communication network 108 and/or any other suitable communication networks. For example, the communications systems 208 can include one or more transceivers, one or more communication chips and/or chip sets, etc. In a more particular example, the communications systems 208 can include hardware, firmware and/or software that can be used to establish a Wi-Fi connection, a Bluetooth connection, a cellular connection, an Ethernet connection, etc.

In some configurations, the memory 210 can include any suitable storage device or devices that can be used to store instructions, values, etc., that can be used, for example, by the processor 202 to present content using the display 204, to communicate with the server 120 via the communications system(s) 208, and the like. The memory 210 can include any of a variety of suitable volatile memory, non-volatile memory, storage, or any suitable combination thereof. For example, the memory 210 can include RAM, ROM, EEPROM, one or more flash drives, one or more hard disks, one or more solid state drives, one or more optical drives, etc. In some configurations, the memory 210 can have encoded thereon a computer program for controlling operation of the computing device 110. In such configurations, the processor 202 can execute at least a portion of the computer program to present content (e.g., MRI images, user interfaces, graphics, tables, and the like), receive content from the server 120, transmit information to the server 120, and the like.

In some configurations, the server 120 can include a processor 212, a display 214, one or more inputs 216, one or more communications systems 218, and/or memory 220. In some configurations, the processor 212 can be a suitable hardware processor or combination of processors, such as a CPU, a GPU, and the like. In some configurations, the display 214 can include a suitable display devices, such as a computer monitor, a touchscreen, a television, and the like. In some configurations, the inputs 216 can include a suitable input devices and/or sensors that can be used to receive user input, such as a keyboard, a mouse, a touchscreen, a microphone, and the like.

In some configurations, the communications systems 218 can include a suitable hardware, firmware, and/or software for communicating information over the communication network 108 and/or any other suitable communication networks. For example, the communications systems 218 can include one or more transceivers, one or more communication chips and/or chip sets, and the like. In a more particular example, the communications systems 218 can include hardware, firmware and/or software that can be used to establish a Wi-Fi connection, a Bluetooth connection, a cellular connection, an Ethernet connection, and the like.

In some configurations, the memory 220 can include any suitable storage device or devices that can be used to store instructions, values, and the like, that can be used, for example, by the processor 212 to present content using the display 214, to communicate with one or more computing devices 110, and the like. The memory 220 can include any of a variety of suitable volatile memory, non-volatile memory, storage, or any suitable combination thereof. For example, the memory 220 can include RAM, ROM, EEPROM, one or more flash drives, one or more hard disks, one or more solid state drives, one or more optical drives, and the like. In some configurations, the memory 220 can have encoded thereon a server program for controlling operation of the server 120. In such configurations, the processor 212 can execute at least a portion of the server program to transmit information and/or content (e.g., MRI data, results of automatic diagnosis, a user interface, and the like) to one or more computing devices 110, receive information and/or content from one or more computing devices 110, receive instructions from one or more devices (e.g., a personal computer, a laptop computer, a tablet computer, a smartphone, and the like), and the like.

In some configurations, the image source 102 can include a processor 222, imaging components 224, one or more communications systems 226, and/or memory 228. In some embodiments, processor 222 can be any suitable hardware processor or combination of processors, such as a CPU, a GPU, and the like. In some configurations, the imaging components 224 can be any suitable components to generate image data corresponding to one or more imaging modes (e.g., T1 imaging, T2 imaging, fMRI, and the like). An example of an imaging machine that can be used to implement the image source 102 can include a conventional MRI scanner (e.g., a 1.5 T scanner, a 3 T scanner), a high field MRI scanner (e.g., a 7 T scanner), an open bore MRI scanner, a CT system, an ultrasound scanner and the like.

Note that, although not shown, the image source 102 can include any suitable inputs and/or outputs. For example, the image source 102 can include input devices and/or sensors that can be used to receive user input, such as a keyboard, a mouse, a touchscreen, a microphone, a trackpad, a trackball, hardware buttons, software buttons, and the like. As another example, the image source 102 can include any suitable display devices, such as a computer monitor, a touchscreen, a television, etc., one or more speakers, and the like.

In some configurations, the communications systems 226 can include any suitable hardware, firmware, and/or software for communicating information to the computing device 110 (and, in some embodiments, over the communication network 108 and/or any other suitable communication networks). For example, the communications systems 226 can include one or more transceivers, one or more communication chips and/or chip sets, and the like. In a more particular example, the communications systems 226 can include hardware, firmware and/or software that can be used to establish a wired connection using any suitable port and/or communication standard (e.g., VGA, DVI video, USB, RS-232, and the like), Wi-Fi connection, a Bluetooth connection, a cellular connection, an Ethernet connection, and the like.

In some configurations, the memory 228 can include any suitable storage device or devices that can be used to store instructions, values, image data, and the like, that can be used, for example, by the processor 222 to: control the imaging components 224, and/or receive image data from the imaging components 224; generate images; present content (e.g., MRI images, a user interface, and the like) using a display; communicate with one or more computing devices 110; and the like. The memory 228 can include any suitable volatile memory, non-volatile memory, storage, or any of a variety of other suitable combination thereof. For example, the memory 228 can include RAM, ROM, EEPROM, one or more flash drives, one or more hard disks, one or more solid state drives, one or more optical drives, and the like. In some configurations, the memory 228 can have encoded thereon a program for controlling operation of the image source 102. In such configurations, the processor 222 can execute at least a portion of the program to generate images, transmit information and/or content (e.g., MRI image data) to one or more the computing devices 110, receive information and/or content from one or more computing devices 110, receive instructions from one or more devices (e.g., a personal computer, a laptop computer, a tablet computer, a smartphone, and the like), and the like.

Figure 3:
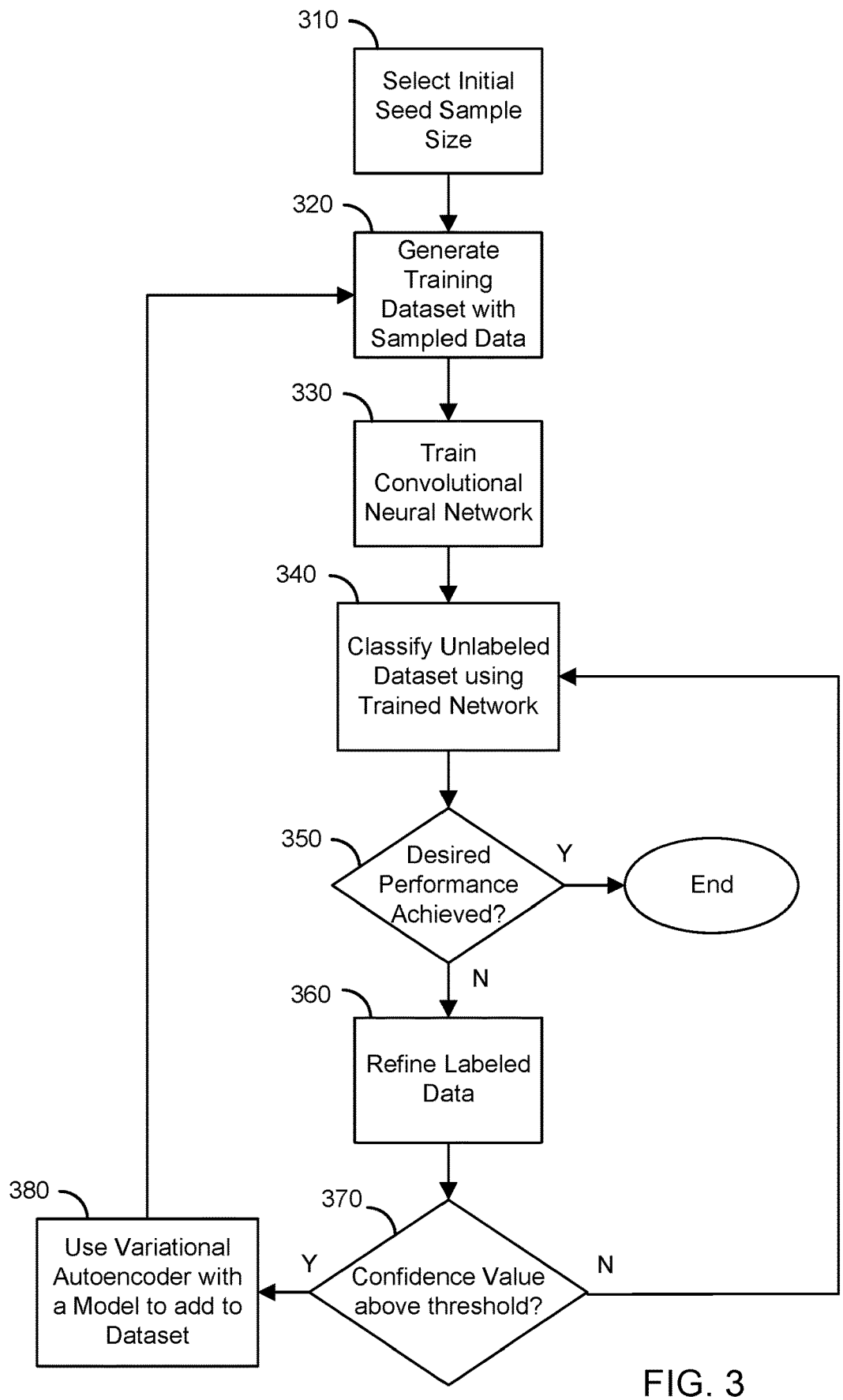
FIG. 3 is a flowchart setting forth some examples of steps for a process in accordance with one aspect of the disclosure.

Referring to FIG. 3, a flowchart is provided setting forth some non-limiting example steps for a method of automatically classifying unstructured imaging data in accordance with the present disclosure. As will be described, the present disclosure provides an iterative snowball sampling that allows for the accurate classification of unstructured imaging data without the need for extensive training datasets that include costly human-annotated information.

In particular, an initial seed sample size is selected at step 310. A training dataset is generated at step 320 with sampled data, which is used to train the convolutional neural network at step 330. In some configurations, the convolutional network is a deep convolutional neural network (DCNN). The trained network classifies unlabeled data at step 340 with the performance evaluated at step 350. If the desired performance is achieved, then the process may end. For example, at step 350, the system may evaluate whether the network's ability to identify a feature in an image exceeds a defined threshold of speed, classification accuracy, reproducibility, efficacy, or other performance metric.

If a desired level of performance is not achieved, then the labeled data may be refined at step 360, by determining if a confidence value for the data is above a certain threshold at step 370. A confidence value may be the same as the desired performance and use the same metrics, or a confidence value may be a classification accuracy that describes the percentage of the time or the frequency with which an image feature or region is identified correctly. If the confidence value does not exceed the threshold, then the network may be used to re-classify the data by repeating the process at step 340. If the confidence value is exceeded, then a VAE with a model, such as a GMM, may be used at step 380 to add the data back into the training dataset and repeat the process from step 320.

In some configurations, the initial seed annotated data sets used to train the DCNN may be small. In these cases, the generated labeled data may contain errors in classification or may be generally unstructured. To prevent this, steps 340-380 may be implemented in an architecture that includes the VAE and GMMs and implements a snowball sampling algorithm to refine the classification. The VAE represents features of the candidate annotated data set (having m data size) into latent space with a Gaussian distribution. The GMMs may then conduct binary clustering within each class across the annotated candidate datasets. Between two clusters consisting of mean and variance vectors, a user may choose the cluster ($c^*$) which is closest to the cluster center ($c$) of the selected seed sample. The data set with the size $\overline{m}$ closest to the cluster center ($c^*$) may be selected. The VAE extracts generic features from each cluster and GMM improves clustering accuracy. This iterative data curation process can increase the quantity of annotated dataset and improve the quality of dataset. This may be repeated for each annotated class.

Specifically, deep learning classification accuracy is historically dependent on the size of the initial training datasets. Quantifying the size of a dataset required to achieve a target accuracy is important when trying to decide the feasibility of a system. In many cases, the limitation of data size presents us from developing robust AI algorithms. Learning curve analysis is one such approach to model classification performance and predict the sample size needed. The learning curve can be conceptualized as an inverse power law function. Classification accuracy (y) is expressed as a function of the training set size (x) and a given unknown parameter (b=(b$_1$, b$_2$, b$_3$)), expressed as the following equation $$y=f(x,b)=b_1+b_2 \cdot x^{b_3} \qquad (1)$$

where x=[x$_1$, x$_2$, . . . , x$_N$]$^T$, y=[y$_1$, y$_2$, . . . , y$_N$]$^T$, b=[b$_1$, b$_2$, b$_3$]$^T$, and N is the number of classes; b$_1$, b$_2$, and b$_3$ represent the bias, learning rate, and decay rate, respectively. The model fit assumes that the classification accuracy (y) grows asymptotically to bi, the maximum achievable classification performance. With the observed classification accuracy at six different sizes of training sets (5, 10, 20, 50, 100, and 200), unknown parameters (b=[b$_1$, b$_2$, b$_3$]T) may be estimated using weighted nonlinear regression, $$E(b) = \sum_{p=1}^{m} w_p \cdot (t_p - y_p)^2 \qquad (2)$$
$$= \sum_{p=1}^{m} w_p \cdot (t_p - f(x_p, y_p))^2$$
$$= \sum_{p=1}^{m} w_p \cdot r_p(b)^2$$
$$= RWR$$

where $t_p$ is the desired output when the input is $x_p$; $y_p$=f($x_p$; b) is the model's output when input is $x_p$; $r_p$(b) is the residual between $t_p$ and $y_p$; and R is the matrix form. The weight terms $w_p$ in the diagonal matrix W can be determined by applications. In some settings, the weighted nonlinear least-squares estimator may be more appropriate than a regular nonlinear regression method to fit the learning curve when measurement errors do not all have the same variance.

Classification accuracy using relatively large sizes of training sets (such as 100 and 200) may have a lower variance than when using smaller sample sizes (such as 5, 10, 20, and 50). The learning curve may therefore be fitted by higher weighting values at the points of larger data set sizes. For example, the weights may be chosen as $w_p$=[1, 1, 1, 1, 100, 150] for a large dataset with a learning curve, but may be $w_p$=[1, 1, 1, 1, 1, 1] for an unweighted nonlinear least-squares estimator.

In one configuration, an autoencoder can be created that has two complementary networks consisting of an encoder and a decoder. The encoder has a multilayer perceptron neural network allowing it to map input x to a latent representation z, and the decoder maps the latent variable z back to a reconstructed input value $\hat{x}$:

$$z \sim f(x) = q_\varphi(z|x)$$
$$\hat{x} \sim g(z) = p_\theta(x|z) \qquad (3)$$

where the tunable parameters φ as encoder and θ as decoder of artificial neural networks are optimized for below the variational lower bound, L(θ, φ, x):

$$L(\theta,\varphi,x) = E_{q_\varphi(x|x)}[\log p_\theta(x|z)] - D_{KL}[q_\varphi(q_\varphi(z|x)\|p_\theta(z)] \qquad (4).$$

The objective of this cost function is to minimize both the generative and the latent losses. Generative loss describes how accurately the decoder network reconstructs images ($\hat{x}$) from a latent vector z, and latent loss is derived from $q_\varphi$(z|x) so that $D_{KL}$[ . . . ] is close to zero. One difference between a typical autoencoder (also called vanilla autoencoder) and a variational autoencoder (VAE) is that variational autoencoders generate latent vectors approximating a unit Gaussian distribution (i.e. z~N(0,I)), whereas vanilla autoencoders generate deterministic latent variables z.

In some configurations, the iterative snowball sampling process for automatic labeling of training data may also be expressed as:

--- i ← 0
$x_s$ ← Select training sample (x) with initial labeled seed size (s)
if i=0: $x_m^j$ ← $x_s$
else: $x_m^j$ ← Classify unlabeled training set (M) by d($x_m^j$) into m labeled candidate set
repeat
   d($x_m^j$) ← Train deep convolutional neural network with $x_m^j$
   f($x_m^j$),g(z) ← Train encoder and decoder of VAE
   z ~ f($x_m^j$) ← Feature representation on latent space of encoder
   c ← Binary clustering using GMMs
   c* ← Select cluster center closest distance to seed data ($x_s$)
   $x_m^j$ ← Select $\overline{m}$ data set size closest to c *
   $\overline{m}$ = $\overline{m}$ + s ← Add new label sets into initial seed
   i ← i+1
until M ← $\overline{m}$

---

In some configurations, the system learns features of input images using a VAE as an unsupervised learning representation, clusters the features by Gaussian mixtures models, and annotates the images by refining candidates pre-labeled or preclassified from the deep convolutional neural network as supervised learning. The DCNN may be trained for body region classification using a small seed training dataset to create larger annotated training datasets by snowball iterative sampling, leading to higher final accuracy. The system may be used to classify images for any part of the human anatomy, and may be used to classify images beyond restricted regions.

Example of Data Set Annotation

In one example of the method and system, experiments were conducted using six different training seed sizes (5, 10, 20, 50, 100, 200/class) on whole body CT images. The fine-tuned DCNN model with snowball sampling was compared with other two common learning methods, the DCNN model trained from scratch and the fine-tuned DCNN model with transfer learning method, to evaluate classification performances. It was observed that the method gave comparable accuracy results (98.79%) from only 100 labeled seed size with the accuracy from 1,000 seed size by the fine-tuned DCNN (98.71%). In the results of this example, the automatic labeling method contributes to saving 90% of labeling efforts in body part classification while preserving the high accuracy.

A database of CT images was compiled from the clinical PACS at a quaternary referral hospital. Preprocessing software was developed to annotate and categorize these images into 6 different body regions: brain, neck, shoulder, chest, abdomen, and pelvis. Only images that could be clearly defined as one of the aforementioned body regions were used. The intervening areas were excluded from training due to their lack of clear regional definition. Each CT examination has a different noise level because of varying radiation dosages, image reconstruction filters, and CT vendors. Image voxels may also have varying pitches because of the differences in the image reconstruction fields. Image slice thickness was thicker than axial voxel pitch, so voxels are anisotropic.

Four training datasets with varying members per class were prepared-unlabeled (M=5000/class), test (1000/class), validation (1000/class), and initial seed data (s=5, 10, 20, 50, 100, and 200/class). The initial seed datasets represent the number of labeled data used to train the DCNNs the first time. An aim was to define the minimum number of cases per class required to annotate larger data sets with comparable accuracy to results from manually labeled conventional training datasets.

Any of a variety of D CNN may be used. In the present example, GoogLeNet was selected as it is an efficient, highly performing DCNN. Testing was performed using the NVIDIA Deep Learning GPU Training System (DIGITS) on a DevBox to train the model using each experimental dataset. GoogLeNet uses 22 convolutional layers including 9 Inception modules and 4 different kernel filters (7×7, 5×5, 3×3, and 1×1). The convolutional filters were trained using a stochastic gradient descent (SGD) algorithm with 0.001 of the base learning rate decreased by three steps based on a stable convergence of loss function. Comparision of the effect of transfer learning on the snowball sampling method was made by training one instance of the DCNN from scratch with random weight initialization and another instance with a preloaded, fine-tuned ImageNet pre-trained model. The snowball sampling procedure was iterated 10 times with each initial seed sample size so that the DCNNs were trained and tested a total of 60 times. During each training step, the validation sets (1000/class) were evaluated and the trained GoogLeNet model with the highest accuracy in the third step of learning rate decay was selected.

Figure 4:
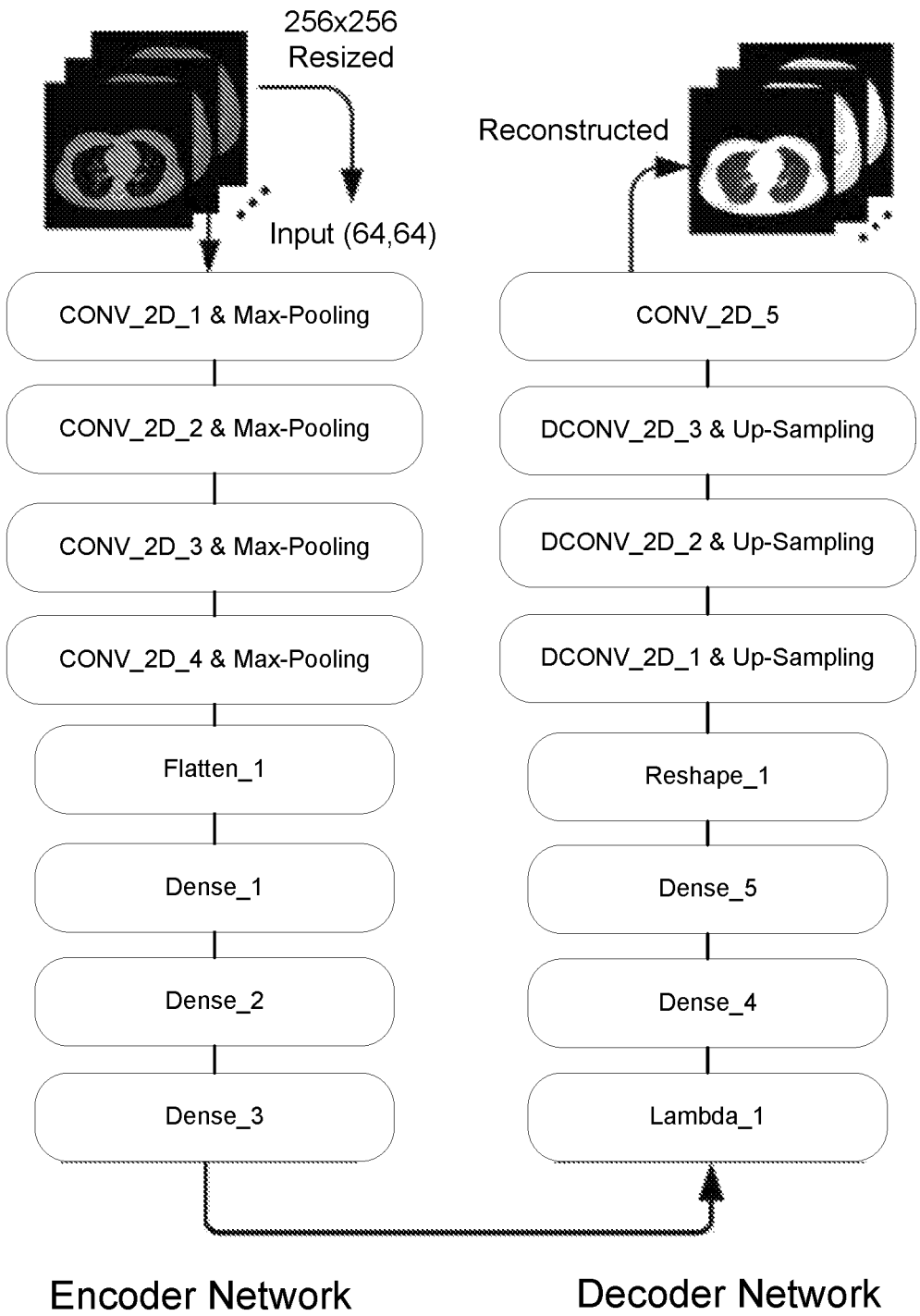
FIG. 4 is a flowchart setting forth some non-limiting examples of steps for a process for utilizing an autoencoder network with four convolutional and deconvolution layers in accordance with one aspect of the present disclosure.

Referring to FIG. 4, at each snowball sampling iteration, the customized VAE was constructed to represent the features of the selected samples. In the illustrated, non-limiting example, the VAE contains four convolutional and deconvolutional layers functioning as encoders and decoders, respectively. One skilled in the art will appreciate that other examples may use more or fewer convolutional or deconvolutional layers, and that any number of layers may be used. Each convolutional layer in the current example had 64 kernel filters (3×3 size) followed by max pooling (2×2). Input images (downscaled to 64×64 from 512×512 for computational efficiency) were compressed to 128-dimensional feature spaces in a Gaussian distribution, ultimately reconstructing the input image using deconvolutional layers and up-sampling layers. The convolutional VAE was implemented using the Keras deep learning library running on a TensorFlow backend. After training the VAE, only the encoder was used as a feature representation, feeding the features into the inputs of Gaussian mixture models (GMMs). Two clusters each having 128-dimenstional Gaussian distributions were generated for each snowball iteration. The cluster ($c^*$) which had the closest distance to the cluster center of the Gaussian distribution of the selected seed sample was selected.

Unlabeled 5,000/class datasets were initially annotated by the DCNNs that were trained with labeled seed data (e.g. 5 examples per class). The labeled candidates were refined by binary clustering using GMMs and finally 500/class ($\bar{m}$=500) at each snowball iteration. Through ten iterations, all unlabeled data sets were labeled. This automatic labeling procedure was conducted according to six different seed sizes (5, 10, 20, 50, 100, and 200/class). During each iteration, annotated image data was added to the next training data pool so that classification accuracy increased gradually. Mislabeled classes were significantly reduced after refining the training. The size of the initial seed influences the overall classification performance, with diminishing returns after 50 cases per class. Each experiment was repeated 10 times by randomly selecting seed samples from labeled training datasets. The trained model was then tested by introducing 1,000 new images of each body class. A total of 6,000 images were used for the performance evaluation in the present example.

For all defined body parts, classification accuracy was at or near 100%. Although the system was not trained on images of transition regions, it was able to infer these areas with considerable accuracy. The network was able to extract and identify similar features at the level of the Inception module despite wide ranges of normal variation in the same anatomic region.

Figure 5:
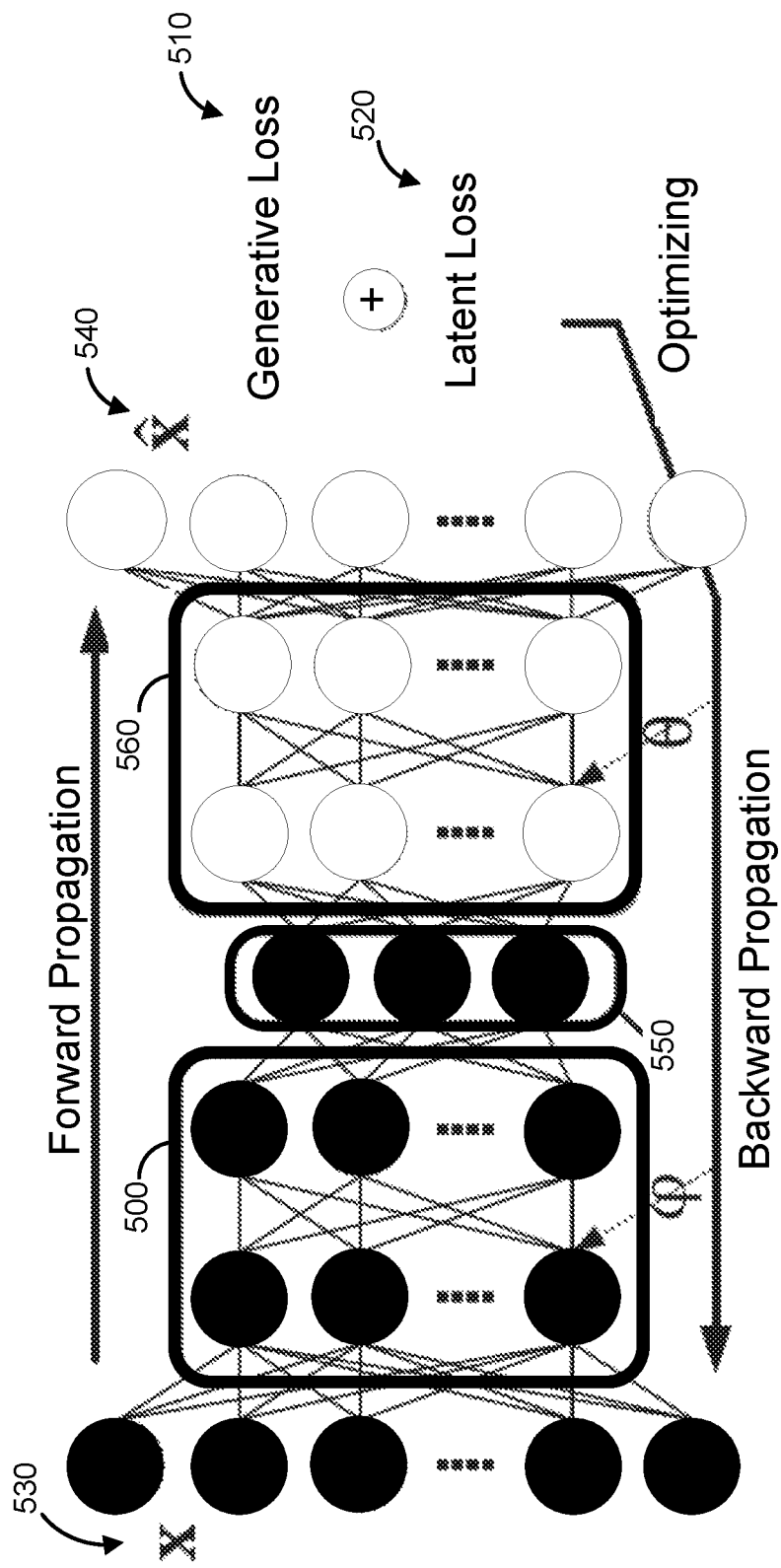
FIG. 5 is a graphic illustration of forward and backward propagation using one configuration of an autoencoder where latent and generative losses are minimized in accordance with the present disclosure.

Referring to FIG. 5, one non-limiting configuration for an autoencoder is shown, where generative loss $\|(x-\hat{x})\|^2$ 510 and latent loss $D_{KL}[N(\mu(x), \sigma(x))\|N(0, I)]$ 520 are controlled and, in some configurations, minimized. With equations 3 and 4, generative loss describes how accurately the decoder network g(z) 560 reconstructs images ($\hat{x}$) 540 from input x 530 and encoder network f(x) 500 through a latent vector z 550, where latent loss is derived from $q_\varphi(z|x)$ so that $D_{KL}[\ldots]$ latent loss 520 is close to zero. Even though the composed neural network has many unknown weights to estimate, the simple cascade structure of multilayer neural network makes it possible to improve the accuracy by iteration. The input can call forward function and calculate loss function. Then the prediction errors are backpropagated to improve system performance.

Figure 6:
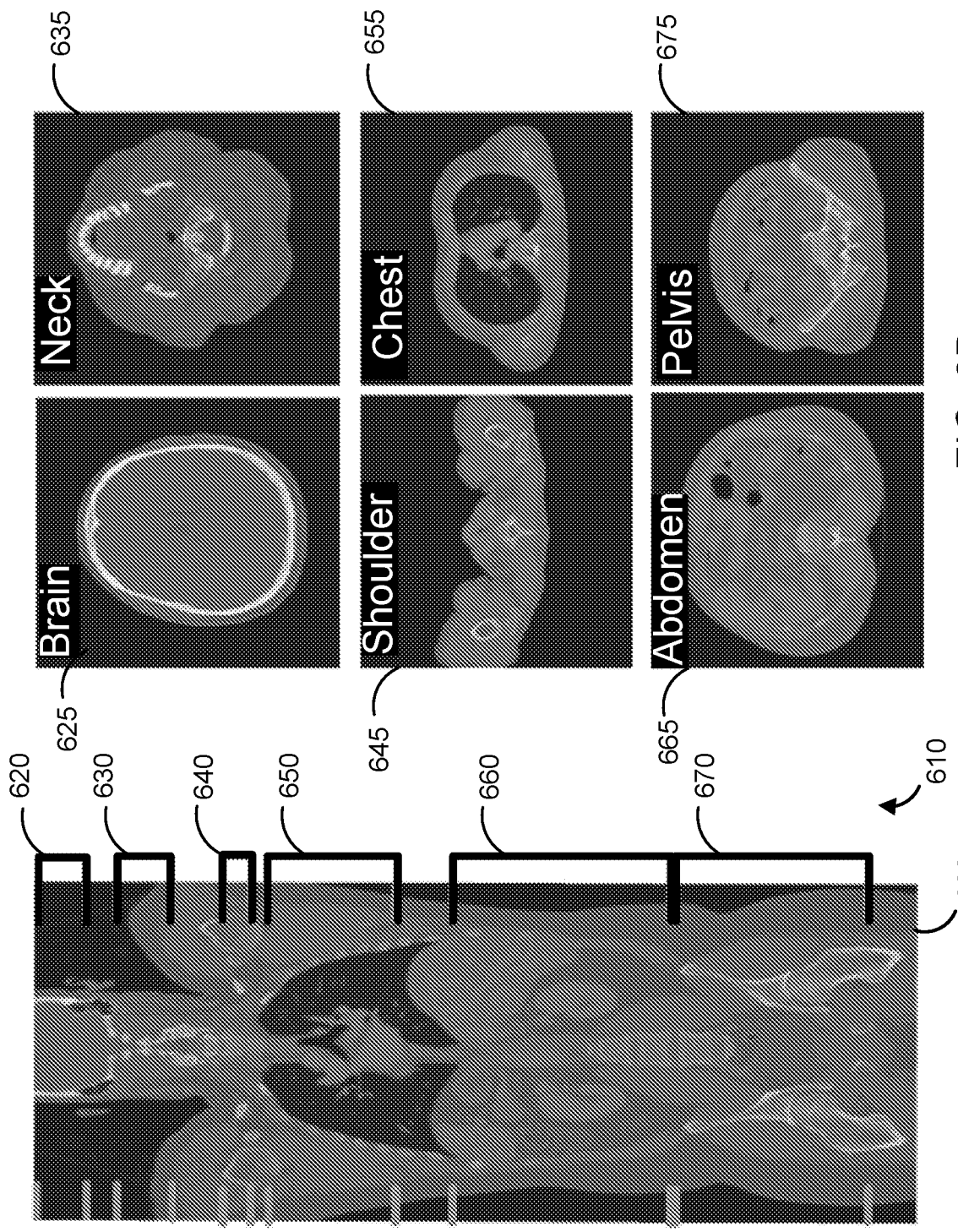
FIG. 6A is an image of a coronal reconstruction of a whole-body CT with each body region identified in accordance with the present disclosure.
FIG. 6B is a panel of axial image slices corresponding to the body regions identified in FIG. 6A in accordance with the present disclosure.

Referring to FIGS. 6A and 6B, an example of body part classification created by the above-described systems and processes is shown. FIG. 6A depicts a whole-body CT image 600, such as may be acquired and provided to the above-described systems. Using the above-described techniques, body part regions 610 can be classified and labeled. Labeling of the data may be performed with a neural network, and refining of the dataset used to train the neural network may be as described above. Then, as illustrated in FIG. 6B, axial CT images corresponding to the body part regions 610 can be selected and labeled. As examples, a brain region 620 has a corresponding axial image 625, a neck 630 has axial image 635, a shoulder 640 has axial image 645, a chest 650 has axial image 655, an abdomen 660 has axial image 665, and a pelvis 670 has axial image 675. Any number of regions 610 may be identified for a subject, and any number of corresponding axial images may be used.

Figure 7:
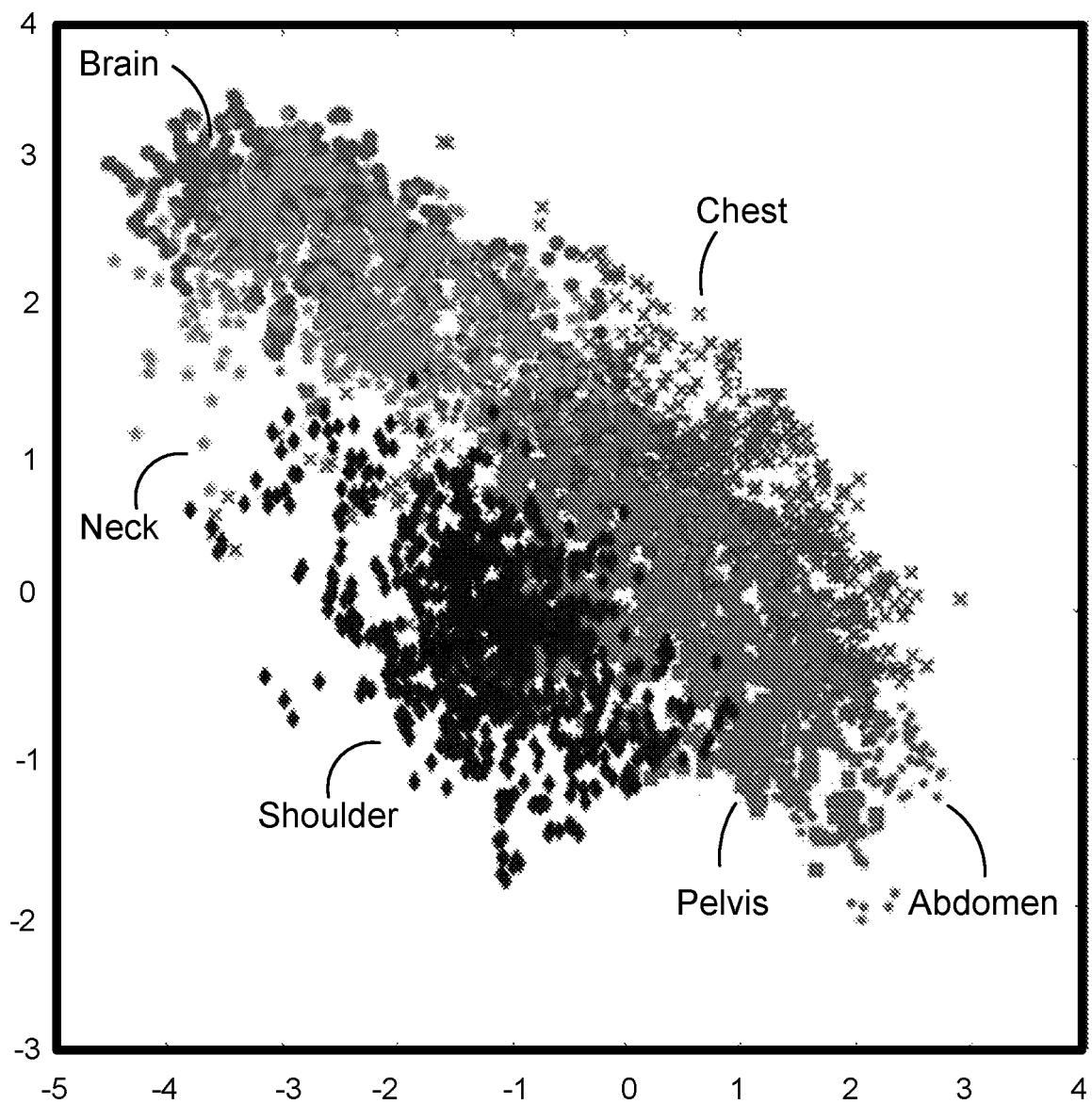
FIG. 7 is a graph providing a scatterplot of feature representations projected onto 2D latent space of a convolutional variational autoencoder in accordance with the present disclosure.

Referring to FIG. 7, a scatter plot of 2D latent space is shown where each cluster of data represents different body regions. For the example data shown in FIG. 7, 128-dimensional latent representations of 6000 cases classified by the convolutional VAE using 200 cases per class were visualized and resulted in 6 body region clusters with areas of overlap. This form of scatter plot display may be used to aid an automated routine in identifying what data corresponds to what body region by accounting for data clustering.

Figure 8:
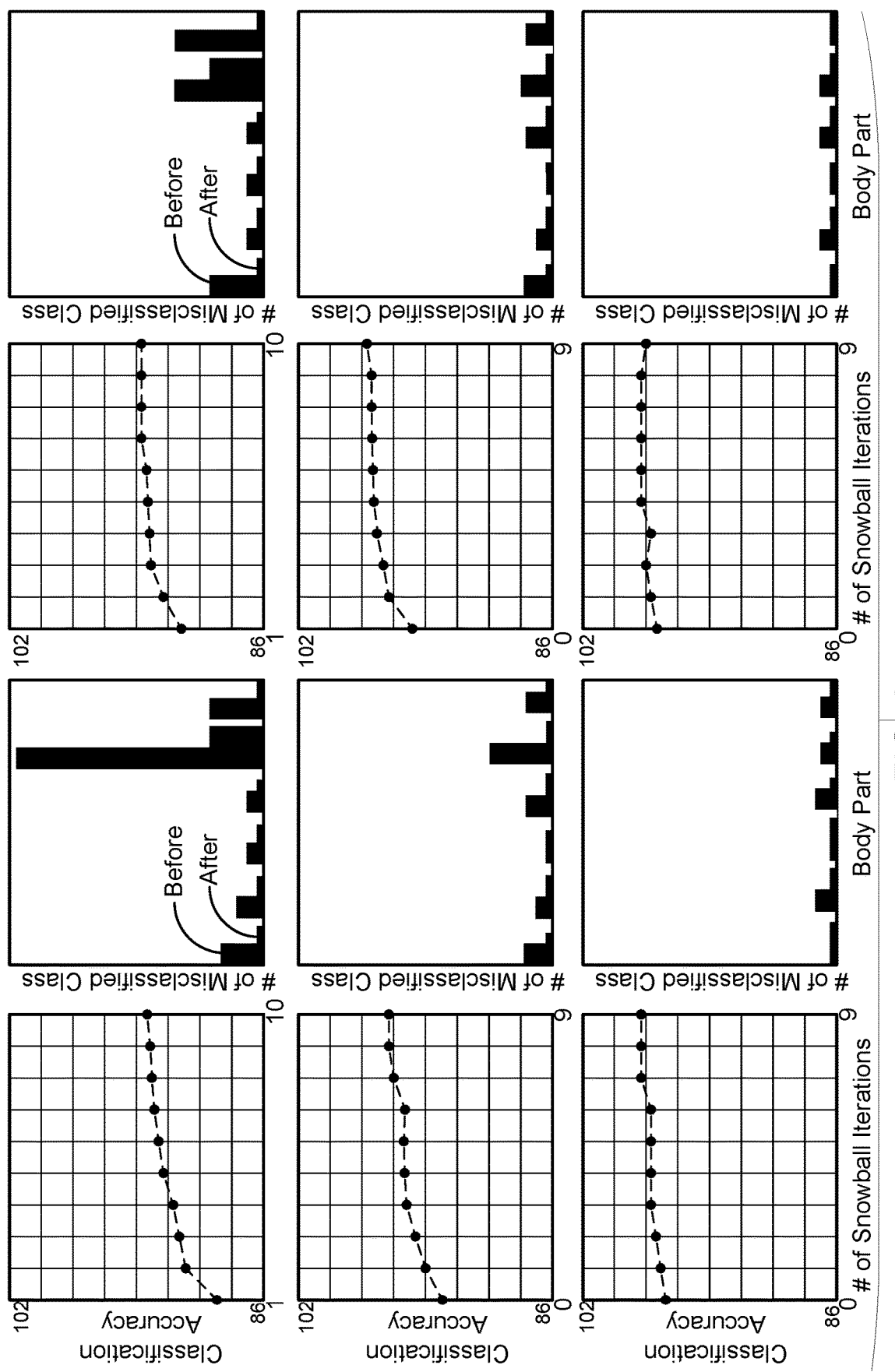
FIG. 8 is a series of correlated graphs of 6 example snowball sampling method reflecting increasing accuracy for increasing iterations in accordance with the present disclosure.

Referring to FIG. 8, an example of fine-tuned DCNN classification accuracy and number of mislabeled classes during ten snowball sampling iterations before and after a refining process by GMMs with six different initial seed sizes are shown. Varying training datasets were annotated using ten snowball iterations from varying initial seeds (5, 10, 20, 50, 100, and 200). During each iteration, annotated image data was added to the next training data pool so that classification accuracy increases gradually, as can be seen in FIG. 8.

Figure 9A:
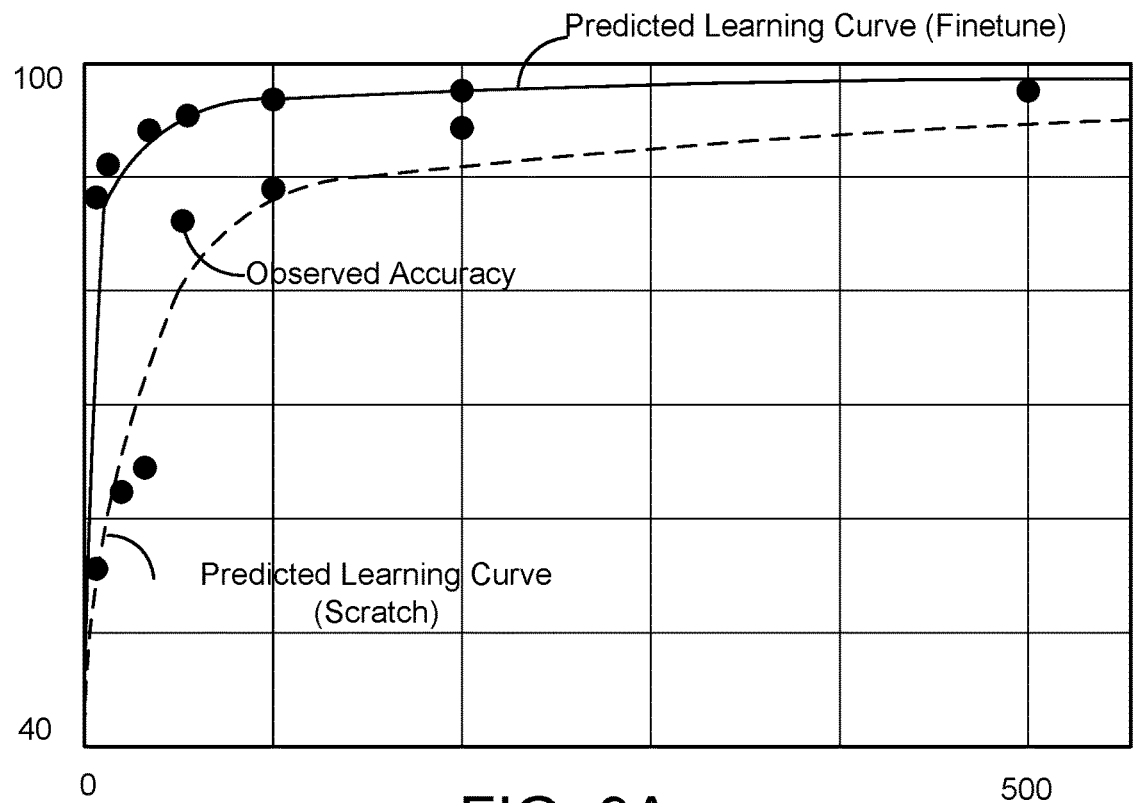
FIG. 9A is a graph of examples of classification accuracy versus a number of snowball sampling iterations in accordance with the present disclosure.
Figure 9B:
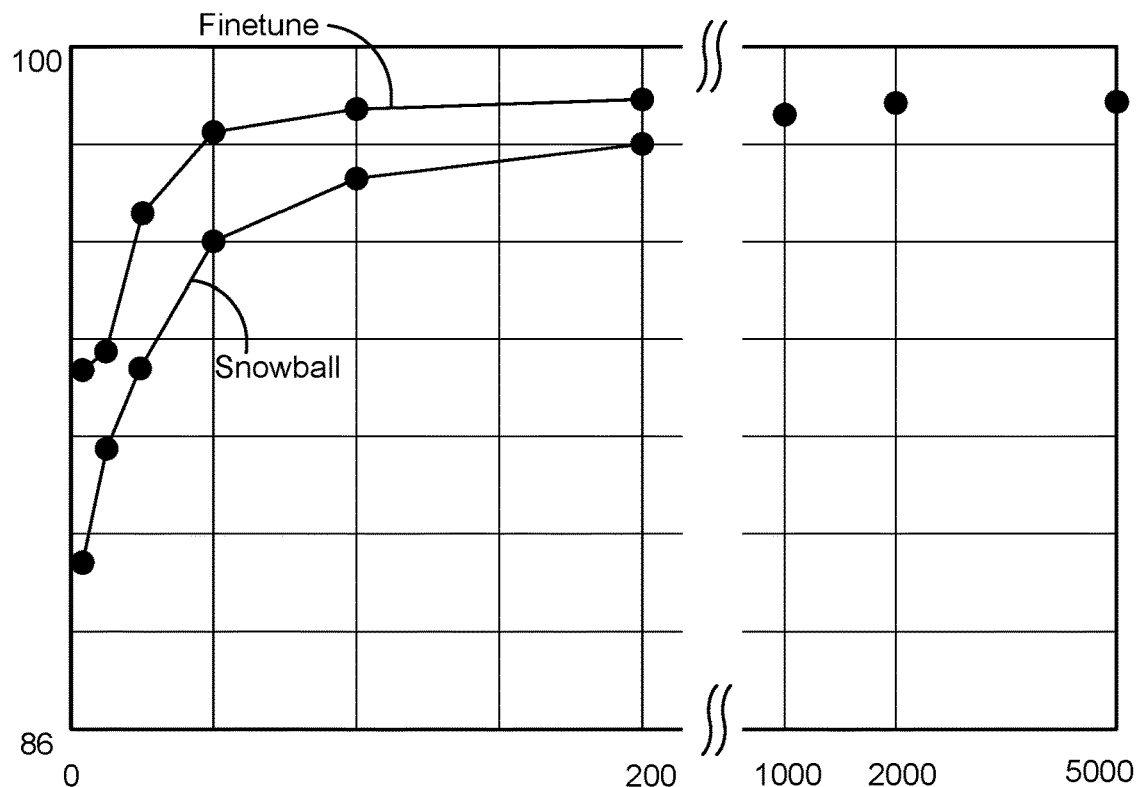
FIG. 9B is a graph of classification accuracy versus training data size for comparing one configuration of a tuned convolutional network with and without snowball sampling in accordance with the present disclosure.

Referring to FIGS. 9A and 9B, examples of classification accuracy are plotted with respect to size of training data or class. FIG. 9A reflects how the fine-tuned DCNN with transfer learning performs better than the DCNN trained from scratch with random weight initialization. Classification accuracy increased rapidly from seed sizes 5 to 50, while accuracy did not increase significantly from seed size 100 to 200. At this point, the learning curve reached a steady state and did not significantly change in accuracy regardless of the seed size. The learning curve predicted 98% classification accuracy with the observed accuracy at 97.25%. FIG. 9A depicts an example learning curve fit to classification accuracy. FIG. 9B depicts an example of classification accuracy by fine-tuned DCNN model without and with the addition of the snowball sampling iteration.

Example of Organ Classifier

There are increasing concerns about radiation exposure risk due to rising computed tomography (CT) exams in medicine. To measure dose from CT procedures, various CT dosimetry metrics have been introduced. The computed tomography dose index (CTDI) and its derivatives, such as volume CT dose index (CTDIvol), is a primary metric that is measured by polymethyl methacrylate (PMMA) standard phantoms with either 16 cm or 32 cm in diameter. However, CTDIvol does not describe the actual dose patient receives in respect to the different weight, body shapes, and sizes, and also does not provide organ dose. To estimate organ dose of individual patients, Monte Carlo simulations have been conducted on phantom models using mathematical description or image voxels, such as the Imaging Performance Assessment of CT scanner (ImPACT) CT patient dosimetry. However, these all organ dose estimate methods do not provide organ specific dose specific to the organ size and shape. In one configuration, a method is provided for machine learning powered personalized patient organ dose, which may take the form of software to estimate each patient's unique organ size and shape. The method can be used to enable organ detection, segmentation, and volume estimation (lungs, liver, kidneys, urinary bladder, muscles, and the like), which may then be used to control or optimize the level of radiation dose to the patients.

Dedicated patient organ dose reports are an important part of modern radiation safety. Current organ dose estimation techniques use Monte Carlo simulations based on phantoms and mathematical description or image voxels. Considering an individual patient's variance in organ position, orientation, and shape, it is often challenging to map a given CT slice to the slab number of a phantom model for accurate organ dose calculation.

$CTDI_{vol}$ may be measured to indicate the CT scanner output. Generally, the $CTDI_{vol}$ measurement is conducted by imaging a 16 cm diameter phantom for head and a 32 cm diameter phantom for body in a given patient CT scan. It is measured by following standard protocols. The $CTID_{vol}$ may be denoted as:

$$CTDI_{vol} = \frac{CTDI_w}{\text{pitch}} \tag{5}$$

$$CTDI_w = \frac{1}{3} CTDI_{100}^{center} + \frac{2}{3} CTDI_{100}^{periphery}$$

-continued $$CTDI_{100} = \frac{1}{nT} \int_{-50\,mm}^{+50\,mm} D(z) dz$$

where n is the number of tomographic sections imaged in a single axial scan, the number of data channels, T is the width of the tomographic section along the z-axis imaged by one data channel, pitch is the ratio of the table feed per rotation.

In some configurations, $CTDI_{vol}$ may be provided by commercial CT scanner manufactures. In one example, the value from a GE LightSpeed VCT scanner is used to estimate organ dose. The corresponding scan parameters have 120 kVp tube voltage, 0.98 mm pitch, 0.5 second(s) rotation time, and 40 mm collimation. At given scan parameters, the normalized $CTDI_w$ (denoted by $_nCTDI_w$) of ImPACT CT dosimetry calculator was 9.5 (mGy/100 mAs) so that $CTDI_w$ is calculated by $_nCTDI_w$*mA*s/100 and finally $CTDI_{vol}$ is determined by dividing $CTDI_w$ by the pitch in the above equation.

Figures 10A, 10B:
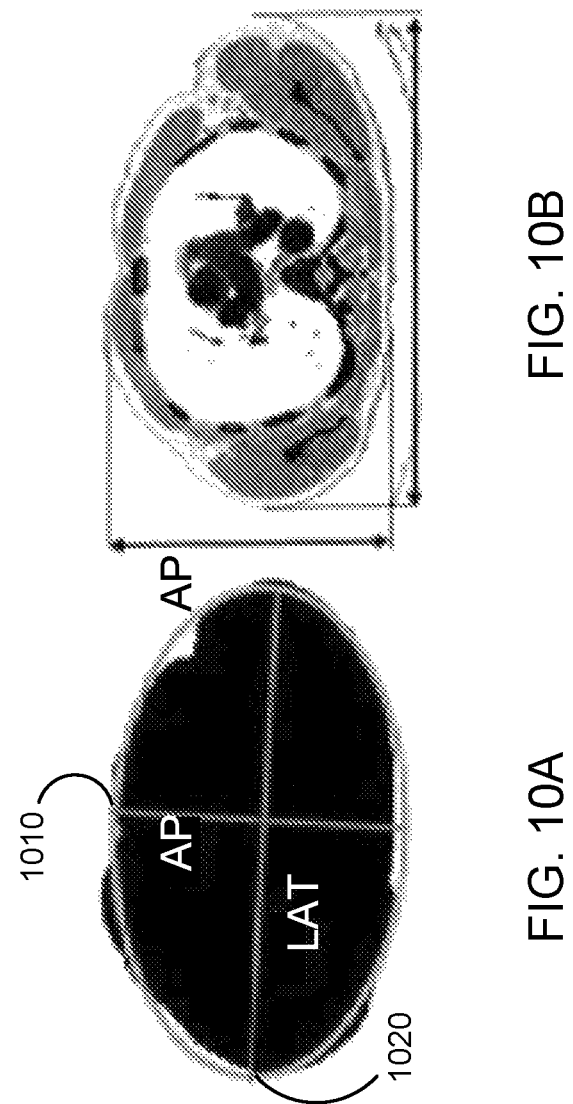
FIG. 10A is an image of a circle whose area is the same as that of a patient cross section from FIG. 10B and which may be used to measure a patient effective diameter in accordance with the present disclosure.
FIG. 10B is an example CT image of a patient cross section.

Referring to FIGS. 10A and 10B, a patient effective diameter may be measured by automatic calculation based on reconstructed axial CT images. FIG. 10B shows a CT image of a patient cross section. FIG. 10A shows the effective diameter, which is defined as the diameter of the circle whose area is the same as that of the patient cross section, assuming patient has elliptical cross sections as indicated in FIGS. 10A and 10B.

$$\text{Effective\_Diameter} = \sqrt{AP \times LAT} \tag{6}$$

where the anterior posterior (AP) dimension 1010 represents the thickness of the body part of the patient and lateral (LAT) dimension 1020 represents the side-to-side dimension of the body part being scanned, respectively. In some configurations, binary morphologic image techniques may be used, such as image dilation and erosion, for estimation of circle of equal area to the patient diameter.

The ImPACT CT dosimetry calculator uses the normalized organ conversion factors, obtained from a Monte Carlo simulation to a mathematical phantom. It has limitation on the calculation of the organ dose of the actual patient, who has different weight and size of body as well as unique organ shape and volumes. In one configuration, to estimate patient organ dose for the various patient weight, a correction factor (CF) may be used at each organ using patient clinical data provided by two different manufacturers. The CF is calculated as:

$$CF^{organ} = \frac{D_{T,RD}^n}{D_{T,IM}^n} \tag{7}$$

where $D_{T,RD}{}^n$ and $D_{T,IM}{}^n$ is the organ dose normalized by $CTDI_{vol}$, which may be provided by the vendor as described previously, such as from eXposure organ dose software of Radimetrics (RD) and ImPACT (IM), respectively.

Figure 11:
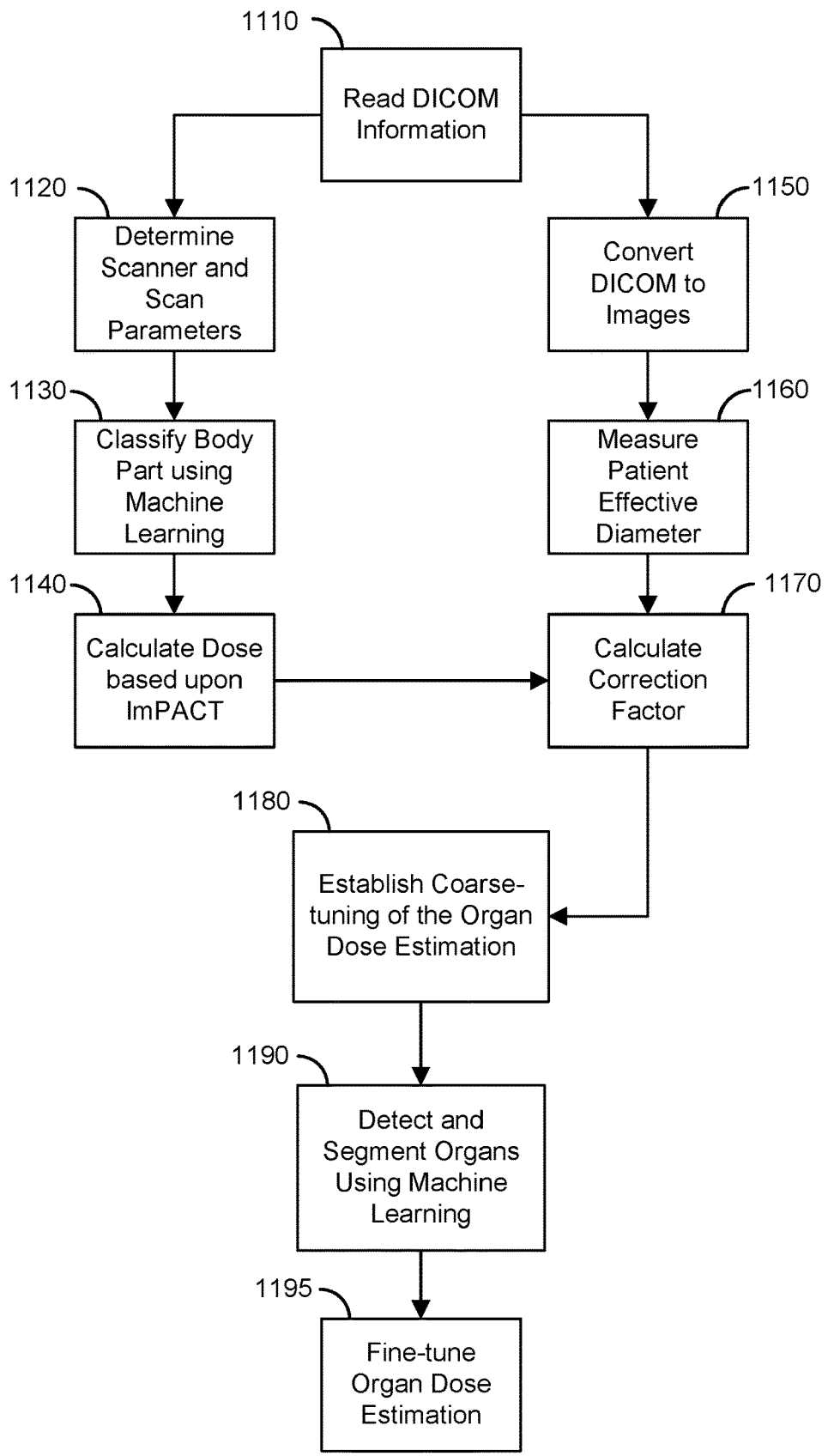
FIG. 11 is a flowchart setting forth some non-limiting examples of steps for one configuration of an organ dose estimation method in accordance with the present disclosure.

Referring to FIG. 11, a flowchart is provided that sets forth some example steps for one configuration of a personalized organ dose estimation (PODE) method. An automated program may be used to extract CT dose information from DICOM metadata and image data at step 1110. The DICOM dose report may be retrieved from a PACS, for example. The report may include $CTDI_{vol}$, dose-length product (DLP), tube current, tube voltage, exposure time, and collimation. The extracted scanner information and scan parameters at step 1120 along with dose-relevant indexes of CT examinations and using machine learning to classify a body part at step 1130 may be used to calculate the organ dose for ImPACT CT dosimetry at step 1140. The DICOM data may be converted to an image at step 1150. The DICOM image may also be written to a standard 8-bit gray image format such as PNG or other formats. A patient effective diameter is calculated at step 1160, and a correction factor as discussed above may be calculated at step 1170. A course-tuning for organ dose estimation may be performed at step 1180. The converted images through scan ranges may be fed to the inputs of a machine learning network, such as a deep convolutional neural net, for use in identifying and segmenting patient organs at step 1190. Organ dose estimates may then be fine-tuned at step 1195 once the organ has been identified and properly segmented by attributing the dose more specifically to the appropriate organs.

In one example, based on the extracted scan parameters, the ImPACT dosimetry calculated 23 organ doses of each patient. The estimated organ dose by ImPACT were corrected by the correction factor (CF) based on a regression model, representing correlation between the ratio of normalized organ dose and patient effective diameter. After the correction of organ dose by considering the patient weights, finally the PODE may be fine-tuned by organ volume and shape through an organ segmentation step.

In one example where each image slice was classified as one of 16 organs, the method may automatically identify which patient organs were included in that scan region for the ImPACT dosimetry calculation. These 16 different organs were identified from axial views of CT images and were labeled. A 22-layer deep CNN using an NVIDIA Deep Learning GPU Training System (DIGITS) was trained and validated with a 646 CT scan dataset. The resultant classified organ was automatically mapped to the slab number of a mathematical hermaphrodite phantom to determine the scan range of ImPACT CT dose calculator.

A dataset of 12,748 CT images of 63 patients was compiled from the clinical PACS (Picture Archiving and Communication System). Preprocessing software was developed to annotate and categorize these images into 16 different body parts in axial views: Brain; Eye Lens; Nose; Salivary Gland; Thyroid; Upper Lung; Thymus; Heart; Chest; Abdomen 1; Abdomen 2; Pelvis 1; Pelvis 2; Urinary Bladder; Genitals; and Leg. Only those of regions that could be clearly defined as one of the aforementioned body parts were used. This is an optimized organ classification choice for the organ dose estimation task. The gaps account for transition regions, which were not used for the training algorithm due to their lack of clear regional definition. Each scan has different background image noise because of radiation dosage level, image reconstruction filter selection, and CT scanner vendors.

In the present example with 16 organ recognition, a GoogLeNet network using 22 convolutional layers including 9 inception modules and 4 sizes of basis or kernel filters (7×7, 5×5, 3×3, and 1×1) was used. 75% of images were used for training and 25% for validation. The GoogLeNet was trained using the NVIDIA toolchain of DIGITS and the DevBox with four TITAN GPUs with 7 TFlops of single precision, 336.5 GB/s of memory bandwidth, and 12 GB of memory. GoogLeNet was trained using a stochastic gradient descent (SGD) algorithm until 150 training epochs. Validation data sets were presented upon every epoch during the training process. The initial learning rate was 0.01 and decreased by three steps according to the convergence to loss function.

A total of 646 patients were included in this retrospective study, with a mean age of 66 years old (range 20-95 years). These patients represented a wide spectrum of body habitus, with a mean weight of 85.6 kg (range, 45-181 kg). FIG. 2 is a representative example of classification results of patient organs after chest CT segmentation. The identified organs were labeled from HEAD (Thyroid) to TRUNK (Abdomen1), a region including both kidneys and liver. Based on organ classification, the corresponding scan range for the ImPACT CT dosimetry calculator was determined. For example, the identified thyroid region (HEADS) was mapped to slab number 171/208 of the adult phantom.

The predicted organ location provided by the deep learning driven software also gives information about the volume of an organ in respect to a given scan region. For example, the thyroid (HEAD 5 region) can be identified in slices 10 to 138 of the present example with 99% accuracy, greatly improving patient-specific radiation dose estimation.

In some configurations, the ratio of normalized organ dose by $CTDI_{vol}$ according to the patient effective diameter may be assessed. The identified organs at a given scan region may have a linear relationship, whereas some organs such as brain, eye lenses, and salivary glands may not be identified by a convolutional neural net classifier so that the organ doses are not correlated to the effective diameter. In the example above, the normalized dose coefficients were decreased as the effective diameter increased for all identified organ regions. By assuming linear relationship ($Y=a_1X+a_0$) between the normalized dose coefficient and the effective diameter, a best fit model on each organ may be fit by the least square estimate (LSE), or by any other appropriate estimates.

It will be appreciated by one skilled in the art that the model may be trained for more organ areas than have been disclosed in the examples, such as covering all organs used in the CT organ dose estimator. These organs may include the pancreas, stomach, gall bladder, and colon, and may facilitate longitudinal organ-specific dose calculations.

The present disclosure has described one or more preferred embodiments, and it should be appreciated that many equivalents, alternatives, variations, and modifications, aside from those expressly stated, are possible and within the scope of the invention.

The invention claimed is:

1. A method for automatically processing unstructured medical imaging data to generate organ classified images, comprising:
   a) acquiring medical image data of a subject;
   b) subjecting the medical image data of the subject to a neural network to generate classified image data;
   c) segmenting the classified image data using the convolutional neural network to generate segmented images that distinguish between at least two different organs in the classified regions in the images;
   d) generating a report of a calculated radiation dose for at least one of the at least two different organs in the segmented images; and
   further comprising measuring an effective diameter for a cross section of the subject based upon the images.

2. The method of claim 1 wherein the calculated radiation dose for the at least one of the at least two different organs is based upon organ volume and shape determined by the effective diameter.

3. The method of claim 1 wherein the report includes the ratio of normalized organ dose by $CTDI_{vol}$ to the patient effective diameter.

4. The method of claim 1 wherein classified image data includes at least one of identifying a brain, eye, nose, salivary gland, thyroid, upper lung, thymus, heart, chest, abdomen, pelvis, urinary bladder, genitals, or a Leg.

5. A method for automatically processing unstructured medical imaging data to generate organ classified images, comprising:
a) acquiring medical image data of a subject;
b) subjecting the medical image data of the subject to a neural network to generate classified image data;
c) segmenting the classified image data using the convolutional neural network to geberate segmented images that distinguish between at least two different organs in the classified regions in the images;
d) generating a report of a calculated radiation dose for at least one of the at least two different organs in the segmented images; and
further comprising calculating a correction factor for generating the report of the calculated radiation dose, wherein the correction factor is calculated at each organ using data provided by two different manufacturers.

6. A method for organ classification for unstructured medical datasets, comprising:
a) acquiring images of a region of a subject and labeling the images to generate a training dataset with the images;
b) training a convolutional neural network with the training dataset;
c) classifying a region in the images using the trained network;
d) segmenting the classified images using the convolutional neural network to generate segmented images that distinguish between at least two different organs in the classified regions in the images;
e) generating a report of a calculated radiation dose for at least one of the at least two different organs in the segmented images; and
further comprising measuring an effective diameter for a cross section of the subject based upon the images.

7. The method of claim 6 wherein the calculated radiation dose for the at least one of the at least two different organs is based upon organ volume and shape determined by the effective diameter.

8. The method of claim 6 wherein the report includes the ratio of normalized organ dose by $CTDI_{vol}$ to the patient effective diameter.

9. The method of claim 6 wherein classifying a region includes at least one of identifying a brain, eye, nose, salivary gland, thyroid, upper lung, thymus, heart, chest, abdomen, pelvis, urinary bladder, genitals, or a Leg.

10. A method for organ classification for unstructured medical datasets, comprising:
a) acquiring images of a region of a subject and labeling the images to generate a training dataset with the images;
b) training a convolutional neural network with the training dataset;
c) classifying a region in the images using the trained network;
d) segmenting the classified images using the convolutional neural network to generate segmented images that distinguish betweeen at least two different organs in the classified regions in the images;
e) generating a report of a claculated radiation does for at least one of the at least two different organs in the segmented images; and
further comprising calculating a correction factor for generating the report of the calculated radiation dose, wherein the correction factor is calculated at each organ using data provided by two different manufacturers.

11. A system for organ classification for unstructured medical datasets, comprising:
a computer system configured to:
i) acquire images of a region of a subject and labeling the images to generate a training dataset with the images;
ii) train a convolutional neural network with the training dataset;
iii) classify a region in the images using the trained network;
iv) segment the classified images using the convolutional neural network to generate segmented images that distinguish between at least two different organs in the classified regions in the images;
v) generate a report of a calculated radiation dose for at least one of the at least two different organs in the segmented images; and
further comprising calculating a correction factor for generating the report of the calculated radiation dose, wherein the correction factor is calculated at each organ using data provided by two different manufacturers.

12. The system of claim 11 wherein classify a region includes at least one of identifying a brain, eye, nose, salivary gland, thyroid, upper lung, thymus, heart, chest, abdomen, pelvis, urinary bladder, genitals, or a Leg.

13. A system for organ classification for unstructured medical datasets, comprising:
a computer system configured to:
i) acquire images of a region of a subject and labeling the images to generate a training dataset with the images;
ii) train a convolutional neural network with the training dataset;
iii) classify a region in the images using the trained network;
iv) segment the classified images using the convolutional neural network to generate segmented images that distinguish between at least two different organs in the classified regions in the images;
v) generate a report of a calculated radiation dose for at least one of the at least two different organs in the segmented images; and
further comprising measuring an effective diameter for a cross section of the subject based upon the images.

14. The system of claim 13 wherein the calculated radiation dose for the at least one of the at least two different organs is based upon organ volume and shape determined by the effective diameter.

15. The system of claim 13 wherein the report includes the ratio of normalized organ dose by $CTDI_{vol}$ to the patient effective diameter.

16. A method for automatically processing unstructured medical imaging data to generate organ classified images, comprising:
a) acquiring medical image data of a subject;
b) subjecting the medical image data of the subject to a neural network to generate classified image data;
c) segmenting the classified image data using the convolutional neural network to generate segmented images that distinguish between at least two different organs in the classified regions in the images;

d) generating a report of a claculated radiation does for at least one of the at least two different organs in the segmented images; and calculating the calculated radiation dose using a correction factor, wherein the correction factor represents a correlation between a ratio of a normalized organ dose for the at least one of the at least two different organs and a patient effective diameter.

* * * * *

UNITED STATES PATENT AND TRADEMARK OFFICE
CERTIFICATE OF CORRECTION

PATENT NO. : 11,615,879 B2
APPLICATION NO. : 16/645240
DATED : March 28, 2023
INVENTOR(S) : Synho Do et al.

It is certified that error appears in the above-identified patent and that said Letters Patent is hereby corrected as shown below:

In the Specification

Column 9, Line 51, "fora" should be --for a--.

Column 9, Line 64, Eq. (4), "$D_{KL}[q_\varphi(q_\varphi(z|x)$" should be --$D_{KL}[q_\varphi(z|x)$--.

Column 10, Line 18, "$x_m{}^j$" should be --$x_m^j$--.

Column 10, Line 19, "else: $x_m{}^j$" should be --else : $x_m^j$--.

Column 10, Line 19, "$d(x_m{}^j)$" should be --$d(x_m^j)$--.

Column 10, Line 22, "$d(x_m{}^j)$" should be --$d(x_m^j)$--.

Column 10, Line 22, "with $x_m{}^j$" should be --with $x_m^j$--.

Column 10, Line 23, "$f(x_m{}^j)$" should be --$f(x_m^j)$--.

Column 10, Line 24, "$f(x_m{}^j)$" should be --$f(x_m^j)$--.

Column 10, Line 26, "$x_m{}^j$" should be --$x_m^j$--.

Column 11, Line 15, "D CNN" should be --DCNN--.

Signed and Sealed this
Sixteenth Day of May, 2023

*Katherine Kelly Vidal*
Katherine Kelly Vidal
*Director of the United States Patent and Trademark Office*

Column 14, Line 3, "$\int_{-50mm}^{+50mm}$" should be --$\int_{-50mm}^{+50mm}$--.

Column 14, Line 54, "$D_{T,RD}{}^n$ and $D_{T,IM}{}^n$" should be --$D_{T,RD}^{n}$ and $D_{T,IM}^{n}$--.

In The Claims

Column 17, Claim 5, Line 13, "geberate" should be --generate--.

Column 17, Claim 10, Line 63, "betweeen" should be --between--.

Column 17, Claim 10, Line 65, "claculated radiation does" should be --calculated radiation dose--.

Column 19, Claim 16, Line 1, "claculated radiation does" should be --calculated radiation dose--.